(12) United States Patent
Dahl et al.

(10) Patent No.: US 10,174,383 B2
(45) Date of Patent: Jan. 8, 2019

(54) METHOD OF ESTIMATING THE AMOUNT OF A METHYLATED LOCUS IN A SAMPLE

(71) Applicant: Vanadis Diagnostics, Sollentuna (SE)

(72) Inventors: Carl Oscar Fredrik Dahl, Sigtuna (SE); Olof John Ericsson, Uppsala (SE); Johan Banér, Stockholm (SE)

(73) Assignee: Vanadis Diagnostics, Sollentuna (SE)

( * ) Notice: Subject to any disclaimer, the term of this patent is extended or adjusted under 35 U.S.C. 154(b) by 561 days.

(21) Appl. No.: 14/814,412

(22) Filed: Jul. 30, 2015

(65) Prior Publication Data

US 2016/0047002 A1    Feb. 18, 2016

Related U.S. Application Data

(60) Provisional application No. 62/037,057, filed on Aug. 13, 2014.

(51) Int. Cl.
  *C12Q 1/683* (2018.01)
  *C12Q 1/6858* (2018.01)
  *C12Q 1/6883* (2018.01)
  *C12Q 1/6886* (2018.01)

(52) U.S. Cl.
  CPC .......... *C12Q 1/6886* (2013.01); *C12Q 1/683* (2013.01); *C12Q 1/6858* (2013.01); *C12Q 1/6883* (2013.01); *C12Q 2600/154* (2013.01); *C12Q 2600/158* (2013.01)

(58) Field of Classification Search
  None
  See application file for complete search history.

(56) References Cited

U.S. PATENT DOCUMENTS

| 8,653,007 | B2 | 2/2014 | Zheng et al. | |
| 2003/0096291 | A1* | 5/2003 | Faham | C12Q 1/6853 435/6.11 |
| 2009/0117573 | A1* | 5/2009 | Fu | C12Q 1/6837 435/6.14 |

(Continued)

FOREIGN PATENT DOCUMENTS

| EP | 1882747 | 1/2008 |
| WO | WO 97/45560 | 12/1997 |

(Continued)

OTHER PUBLICATIONS

Goransson et al. Nucleic Acids Research 2009; 37: e7. (Year: 2009).*

(Continued)

*Primary Examiner* — Angela M. Bertagna
(74) *Attorney, Agent, or Firm* — James S. Keddie; Bozicevic, Field & Francis LLP

(57) ABSTRACT

A method of estimating the amount of a methylated locus is provided. In certain embodiments the method comprises: digesting a nucleic acid sample that contains both unmethylated and methylated copies of a genomic locus with an MspJI family member to produce a population of fragments that are in the range of 20-40 nucleotides in length, ligating adaptor sequence A and adaptor sequence B to the respective ends of a target fragment of sequence X, and quantifying the amount of ligation products of formula A-X-B. A kit for performing the method is also provided.

17 Claims, 4 Drawing Sheets

(56) References Cited

U.S. PATENT DOCUMENTS

| | | | | |
|---|---|---|---|---|
| 2010/0167942 A1* | 7/2010 | Zheng | ............... | C12Q 1/6827 |
| | | | | 506/8 |
| 2012/0021919 A1* | 1/2012 | Scholl | ............... | C12Q 1/6876 |
| | | | | 506/2 |
| 2013/0029852 A1* | 1/2013 | Rava | ............... | C12Q 1/6806 |
| | | | | 506/2 |
| 2013/0338933 A1* | 12/2013 | Deciu | ............... | G06F 19/22 |
| | | | | 702/20 |

FOREIGN PATENT DOCUMENTS

| | | |
|---|---|---|
| WO | WO 03/038120 | 5/2003 |
| WO | WO 2006/088978 | 8/2006 |
| WO | WO 2008/119765 | 10/2008 |
| WO | WO 2008/156536 | 12/2008 |
| WO | WO 2009/002891 | 12/2008 |
| WO | WO 2010/113088 | 10/2010 |
| WO | WO 2013/097060 | 7/2013 |
| WO | WO2015083001 | 6/2015 |

OTHER PUBLICATIONS

Dhanasekaran et al. Journal of Immunological Methods 2010; 354: 34-39. (Year: 2010).*
Huang et al. BMC Genetics 2013; 14: 56 (Year: 2013).*
Cohen-Karni, et al. "The MspJI family of modification-dependent restriction endonucleases for epigenetic studies", 11040-11045, PNAS, 2011, vol. 108, No. 27.
Zheng, et al. "A unique family of Mrr-like modification-dependent restriction endonucleases", Nucleic Acids Research, 2010, vol. 38, No. 16 5527-5534.

* cited by examiner

METHOD OF ESTIMATING THE AMOUNT OF A METHYLATED LOCUS IN A SAMPLE

CROSS-REFERENCING

This application claims the benefit of U.S. provisional patent application Ser. No. 62/037,057, filed on Aug. 13, 2014, which application is incorporated by reference for all purposes.

BACKGROUND

5-Methylcytosine is a methylated form of the DNA base cytosine that is believed to be involved in transcriptional regulation. When cytosine is methylated, the DNA maintains the same sequence, but the expression of methylated genes can be altered.

The function of this chemical varies significantly among species: in bacteria, 5-methylcytosine can be found at a variety of sites, and is often used as a marker to protect DNA from being cut by native methylation-sensitive restriction enzymes; in plants, 5-methylcytosine occurs at CpG, CpHpG and CpHpH sequences (where H=A, C or T); and, in fungi and animals, 5-methylcytosine predominantly occurs at CpG dinucleotides. Most eukaryotes methylate only a small percentage of these sites, but 70-80% of CpG cytosines are methylated in vertebrates.

Cytosine methylation in vertebrates typically occurs at CpG sites (cytosine-phosphate-guanine sites, that is, where a cytosine is directly followed by a guanine in the DNA sequence). The formation of Me-CpG is catalyzed by the enzyme DNA methyltransferase. About 80-90% of CpG sites are methylated in human DNA, but there are certain areas, known as CpG islands, wherein none of the CpG dinucleotides are methylated. These are associated with the promoters of 56% of mammalian genes, including all ubiquitously expressed genes. One to two percent of the human genome are CpG clusters, and there is an inverse relationship between CpG methylation and transcriptional activity.

The method described herein provides a way to estimate the amount of a methylated locus in a sample.

SUMMARY

A method of estimating the amount of a methylated locus in a sample is provided. In certain embodiments, the method may comprise: (a) digesting a nucleic acid sample that contains both unmethylated and methylated copies of a genomic locus with an MspJI family member to produce a population of fragments that are in the range of 20-40 base pairs in length and have a central methylated cytosine; (b) ligating adaptor sequence A and adaptor sequence B to the respective ends of a target fragment of sequence X by: (i) hybridizing a splint oligonucleotide of formula B'-X'-A' to the fragments of (a) in the presence of the adaptor sequences A and B, wherein X', A' and B' are complementary to X, A and B, respectively, and (ii) ligating adaptor sequence A, sequence X and adaptor sequence B to one another to produce a product of formula A-X-B; and (c) quantifying the amount of ligation products of formula A-X-B, thereby providing an estimate of the amount of the methylated locus in the nucleic acid sample.

The quantifying may be done using any convenient method, including by qPCR or by sequencing. In some embodiments, the adaptor sequences A and B may be present in the same oligonucleotide molecule and the product of step (b) is a circular nucleic acid molecule. In these embodiments, the quantifying may be done by (i) amplifing the circular nucleic acid molecule by rolling circle amplification (RCA), (ii) hybridizing the RCA product to a population of labeled oligonucleotides that hybridize to multiple positions in the RCA product; and (iii) individually counting the number of labeled RCA complexes.

As will be discussed in greater detail below, in certain cases the method may be used to estimate the amount of fetal DNA in a sample of cell-free DNA from a pregnant female.

A kit for performing the method is also provided.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
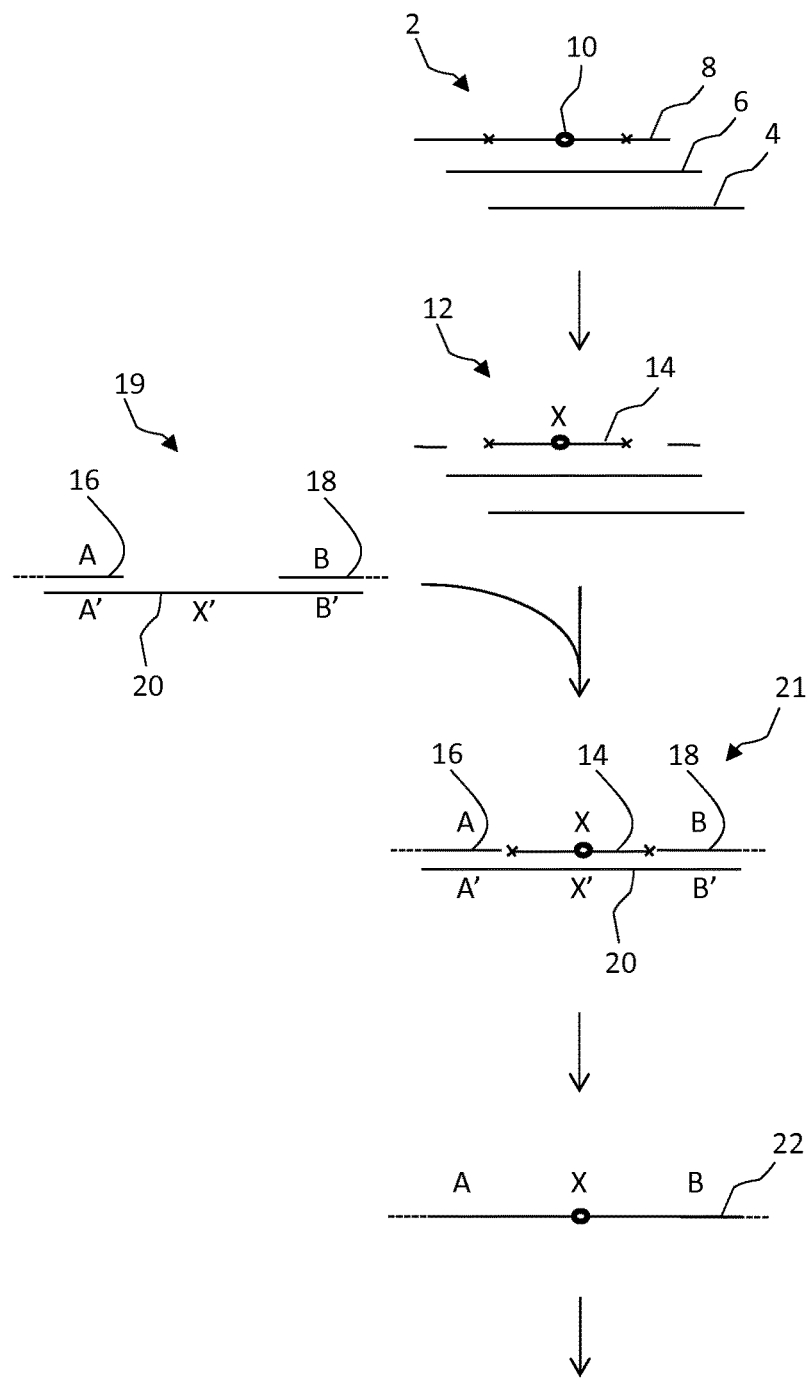
FIG. 1 schematically illustrates some of the features of an embodiment of the subject method.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "genomic locus" refers to a defined region in a genome. A genomic locus exists at the same location in the genomes of different cells from the same individual, or in different individuals. A genomic locus in one cell or individual has a nucleotide sequence that is identical or very similar (i.e., more than 99% identical) to the same genomic locus in a different cell or individual. The difference in nucleotide sequence between the same locus in different cells or individuals may be due to one or more nucleotide substitutions. A genomic locus may be defined by genomic coordinates, by name, or using a symbol.

As used herein, the term "methylation state" refers to the presence or absence of a methyl group on a cytosine residue at a site of methylation. For clarity, a cytosine that is unmethylated will be referred to as "unmethylated cytosine" or "unmethylated C", and a cytosine that is methylated (i.e., 5-methylcytosine) will be referred to as "methylated cytosine", methylated "C" or "methyl C".

As used herein, a "site of methylation" refers to the position of a cytosine nucleotide that is known to be at least sometimes methylated in a genomic locus. The cytosine at a site of methylation can be an unmethylated cytosine or a methylated cytosine. In other words, the term "site of methylation" refers to a specific cytosine in a genomic locus that can be in a methylated state. The site of methylation may be defined by genomic coordinates, or coordinates relative to the start codon of a gene, for example.

The term "corresponds to" and grammatical equivalents, e.g., "corresponding", as used herein refers to a specific relationship between the elements to which the term refers. For example, an oligonucleotide that corresponds to a sequence in a longer nucleic acid contains the same nucleotide sequence as or is complementary to a nucleotide sequence in the nucleic acid.

In the context of a nucleotide in an oligonucleotide that corresponds to a site of methylation or a nucleotide in an oligonucleotide that corresponds to a methylated cytosine, the term "corresponds to" and grammatical equivalents thereof are intended to identify the nucleotide that is correspondingly positioned relative to (i.e., positioned across from) a site of methylation when the two nucleic acids (e.g., an oligonucleotide and genomic DNA containing a methylated cytosine) are aligned or base paired. Again, unless otherwise indicated (e.g., in the case of a nucleotide that "does not base pair" or "base pairs" with a particular residue) a nucleotide that "corresponds to" a site of methylation base pairs with either a methylated site or an unmethylated site. For clarity, in an oligonucleotide, a G or C nucleotide at a position that corresponds to a methylated cytosine in a sequence, e.g., a genomic locus, can: a) base pair with a methylated cytosine in the sequence, b) base pair with a cytosine that positionally corresponds to the methylated cytosine in an amplified version of the sequence, or c) base pair with a G residue that is complementary to such a cytosine in an amplified sequence.

As used herein, a "sequence that is methylated" is a nucleotide sequence that contains a site of methylation, i.e., a cytosine nucleotide that is known to be at least sometimes methylated.

As used herein, the term "unmethylated", with reference to a nucleotide sequence, refers to the copies of a sequence that are not methylated.

As used herein, the term "methylated", with reference to a nucleotide sequence, refers to copies of a sequence that contain 5-methylcytosine. Methylation of a genomic locus may, e.g., alter the expression of a protein, which causes a phenotypic change (e.g., a cancer-related phenotype) in the cells that have such a methylated locus. Alternatively, methylation of a genomic locus may be silent.

A sample that comprises "both unmethylated and methylated copies of a genomic locus" and grammatical equivalents thereof, refers to a sample that contains multiple DNA molecules of the same genomic locus, where the sample contains both unmethylated copies of the genomic locus and methylated copies of the same locus. In this context, the term "copies" is not intended to mean that the sequences were copied from one another. Rather, the term "copies" is intended to indicate that the sequences are of the same locus in different cells or individuals. In other words, a sample contains a mixture of nucleic acid molecules having the same nucleotide sequence, except that some of the molecules contain methylated cytosine residues.

As used herein, the term "degree of methylation" refers to the relative number, percentage, or fraction of members of a particular target nucleotide species within a sample that are methylated compared to those members of that particular target nucleotide species that are not methylated.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "target polynucleotide," as used herein, refers to a polynucleotide of interest under study. In certain embodiments, a target polynucleotide contains one or more sequences that are of interest and under study.

The term "oligonucleotide" as used herein denotes a single-stranded multimer of nucleotides of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The term "primer" as used herein refers to an oligonucleotide that is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be single-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The primers herein are selected to be substantially complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42 C in 50% formamide, 5×SSC, 5× Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together. The term "amplifying" as used herein refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein. An amplification reaction can be isothermal (e.g., in the case of rolling circle amplification) or may require thermocycling (in the case of PCR).

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "partitioning", with respect to a genome, refers to the separation of one part of the genome from the remainder of the genome to produce a product that is isolated from the remainder of the genome. The term "partitioning" encompasses enriching.

The term "genomic region", as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example. Such an oligonucleotide may be employed in an assay that uses a sample containing a test genome, where the test genome contains a binding site for the oligonucleotide.

The term "genomic sequence", as used herein, refers to a sequence that occurs in a genome.

The term "genomic fragment", as used herein, refers to a region of a genome, e.g., an animal or plant genome such as the genome of a human, monkey, rat, fish or insect or plant. A genomic fragment may be an entire chromosome, or a fragment of a chromosome.

The term "affinity tag", as used herein, refers to moiety that can be used to separate a molecule to which the affinity tag is attached from other molecules that do not contain the affinity tag. An "affinity tag" is a member of a specific binding pair, i.e. two molecules where one of the molecules through chemical or physical means specifically binds to the other molecule. The complementary member of the specific binding pair, referred to herein as a "capture agent" may be immobilized (e.g., to a chromatography support, a bead or a planar surface) to produce an affinity chromatography support that specifically binds the affinity tag. In other words, an "affinity tag" may bind to a "capture agent", where the affinity tag specifically binds to the capture agent, thereby facilitating the separation of the molecule to which the affinity tag is attached from other molecules that do not contain the affinity tag.

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-LC-Biotin, -SLC-Biotin or -PEG$_n$-Biotin where n is 3-12.

The term "terminal nucleotide", as used herein, refers to the nucleotide at either the 5' or the 3' end of a nucleic acid molecule. The nucleic acid molecule may be in double-stranded form (i.e., duplexed) or in single-stranded form.

The term "ligating", as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity and in certain cases may have one, two or three non-complementary bases.

The term "digesting" is intended to indicate a process by which a nucleic acid is cleaved by a restriction enzyme. In order to digest a nucleic acid, a restriction enzyme and a nucleic acid containing a recognition site for the restriction enzyme are contacted under conditions suitable for the restriction enzyme to work. Conditions suitable for activity of commercially available restriction enzymes are known, and supplied with those enzymes upon purchase.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "separating", as used herein, refers to physical separation of two elements (e.g., by size or affinity, etc.) as well as degradation of one element, leaving the other intact.

The term "reference chromosomal region," as used herein refers to a chromosomal region of known nucleotide sequence, e.g. a chromosomal region whose sequence is deposited at NCBI's Genbank database or other databases, for example.

The term "strand" as used herein refers to a nucleic acid made up of nucleotides covalently linked together by covalent bonds, e.g., phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "covalently linking" refers to the production of a covalent linkage between two separate molecules, e.g., the top and bottom strands of a double stranded nucleic acid. Ligating is a type of covalent linking.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the melting temperature of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). Nucleic acids may also be denatured chemically (e.g., using urea or NaOH).

As used herein, the term "label" refers to any atom or molecule that can be used to provide a detectable (preferably quantifiable) effect, and that can be attached to a nucleic acid or protein. Labels include but are not limited to dyes and radiolabels such as $^{32}$P; binding moieties such as biotin; haptens such as digoxigenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of a nucleic acid or a protein sequence, so long as the sequence comprising the label is detectable.

The term "labeled oligonucleotide", as used herein, refers to an oligonucleotide that has an affinity tag (e.g., a biotin moiety), an oligonucleotide modified with atoms or groups enabling separation or detection (e.g., bromo-deoxyuridine, or colloidal gold particles conferring different density), and an oligonucleotide modified with or an optically detectable label (e.g., a fluorescence or another type of light emitting label). Oligonucleotides that contain only naturally occurring nucleotides are not labeled oligonucleotides.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide is obtained.

The term "next-generation sequencing" refers to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies.

The term "extending", as used herein, refers to the extension of a primer by the addition of nucleotides using a polymerase. If a primer that is annealed to a nucleic acid is extended, the nucleic acid acts as a template for an extension reaction.

The term "clonal PCR" is a PCR technique in which each reaction is done on a single template molecule, and the PCR reactions are kept spatially separated from one another. Bridge PCR and emulsion PCR, commonly used in next generation sequencing applications, are examples of clonal PCR.

The term "bridge PCR" refers to a solid-phase polymerase chain reaction in which the primers that are extended in the reaction are tethered to a substrate by their 5' ends. During amplification, the amplicons form a bridge between the tethered primers. Bridge PCR (which may also be referred to as "cluster PCR") is used in Illumina's Solexa platform. Bridge PCR and Illumina's Solexa platform are generally described in a variety of publications, e.g., Gudmundsson et al (Nat. Genet. 2009 41:1122-6), Out et al (Hum. Mutat. 2009 30:1703-12) and Turner (Nat. Methods 2009 6:315-6), U.S. Pat. No. 7,115,400, and US application publication Nos. US20080160580 and US20080286795. Bridge PCR is a type of "clonal PCR", i.e., is a PCR technique in which each reaction is begun on a single template molecule, and the PCR reactions are kept spatially separated from one another.

The term "barcode sequence" or "molecular barcode", as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). A barcode sequence may be at the 5'-end, the 3'-end or in the middle of an oligonucleotide. Barcode sequences may vary widely in size and composition; the following references provide guidance for selecting sets of barcode sequences appropriate for particular embodiments: Brenner, U.S. Pat. No. 5,635, 400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

The term, "intramolecularly ligating" refers to a ligation in which the 5' end and the 3' end of a strand of nucleic acid are ligated to one another to produce a circular DNA molecule.

As used herein, the term "MspJI family restriction endonuclease" refers to a family of restriction endonucleases that recognize methylated cytosine and generate a double stranded break in the DNA molecule at a site that is upstream or downstream from the methylated cytosine. These enzymes do not cleave unmethylated DNA. If both strands of the DNA are methylated (which is commonly the case in CpG methylation) then the enzyme will cut the DNA to produce a fragment of 20-40 base pairs in length, depending on the enzyme used. MspJI, for example, recognizes each hemi-methylated site individually and cleaves bidirectionally to generate 32-base or 31-base fragments, respectively. These fragments contain the central methylated site and have 4-base 5' overhangs at each end. The MspJI family of endonucleases is described in, e.g., Zheng et al (Nucleic Acids Res. 2010 A unique family of Mrr-like modification-dependent restriction endonucleases. 38: 5527-34) and Cohen-Karni (Proc. Natl. Acad. Sci. 2011 The MspJI family of modification-dependent restriction endonucleases for epigenetic studies 108:11040-5) and US20100167942, which are incorporated by reference for details of this family of enzymes. Examples of MspJI family restriction endonucleasse include FspEI, LpnPI, AspBHI, RlaI, and SgrTI. Reference to a MspJI family member, either generically or by name, is intended to refer to a wild type restriction endonuclease as well as variants that have an amino acid sequence that is at least 90% (e.g., at least 95%) identical to the wild type restriction endonuclease.

As used herein, the term "population of fragments that are in the range of 20-40 base pairs in length" refers to a mixture of digestion fragments. The fragments have a central cytosine residue (which is part of the recognition site for the MspJI family endonuclease) and have 3' or 5' overhangs, depending on which enzyme is used.

As used herein, the term "respective ends", in the phrase "ligating adaptor sequence A and adaptor sequence B to the respective ends of a target fragment" is intended to mean that sequence A is added to one end of the target fragment and sequence B is added to the other end of the target fragment.

Certain polynucleotides described herein may be referred by a formula (e.g., "B'-X'-A'" and "A-X-B"). Such formulas follow the established convention in that they describe a polynucleotide that is oriented in the 5' to 3' direction. The components of the formula, e.g., "A", "X" and "B" refer to separately definable sequences of nucleotides within a polynucleotide, where the sequences are linked together covalently such that a polynucleotide described by a formula is a single molecule. In many cases the components of the formula are immediately adjacent to one another in the single molecule. Following convention, the complement of a sequence shown in a formula will be indicated with a prime (') such that the complement of sequence "A" will be "A'". Moreover, unless otherwise indicated or implicit from the context, a polynucleotide defined by a formula may have additional sequence, a primer binding site, a molecular barcode, a promoter, or a spacer, etc., at its 3' end, its 5' end or both the 3' and 5' ends.

As used herein, the term "adaptor sequences A and B" refers to different sequences.

As used herein, the term "ligatably adjacent" in the context of two oligonucleotide sequences that are ligatably adjacent to one another, means that there are no intervening nucleotides between two oligonucleotides and they can be ligated to one another.

As used herein, the term "splint oligonucleotide", as used herein, refers to an oligonucleotide that, when hybridized to two or more other polynucleotides, acts as a "splint" to position the polynucleotides next to one another so that they can be ligated together, as illustrated in FIG. 1.

As used herein, the term "a circular nucleic acid molecule" refers to a strand that is in the form of a closed circle that has no free 3' or 5' ends.

As used herein, the term "fetal fraction" refers to the percentage of cell free DNA from a developing fetus in the maternal bloodstream of a pregnant female.

Other definitions of terms may appear throughout the specification.

DESCRIPTION OF EXEMPLARY EMBODIMENTS

A method of estimating the amount of a methylated locus is provided. In certain embodiments the method comprises: digesting a nucleic acid sample that contains both unmethylated and methylated copies of a genomic locus with an MspJI family member to produce a population of fragments that are in the range of 20-40 nucleotides in length, ligating adaptor sequence A and adaptor sequence B to the respective ends of a target fragment of sequence X, and quantifying the amount of ligation products of formula A-X-B. A kit for performing the method is also provided.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

With reference to FIG. 1, some embodiments of the method comprise digesting a nucleic acid sample 2 that contains both unmethylated (4 and 6) and methylated copies (8) of a genomic locus using an MspJI family restriction endonuclease. As illustrated, if the recognition sequence is methylated on both strands (indicated by the filled circle 10), then the enzyme will cleave on both sides of the recognition sequence, as indicated by the x's in fragment 8. This digest produces digested sample 12 that comprises a population of fragments that are in the range of 20-40 base pairs in length and have a central methylated cytosine. As would be apparent, the initial sample being digested is not an amplified sample. If genomic DNA is digested, the digested sample should contain at least several thousand, if not at least at least 10,000 or 100,000 or more, fragments that are 20-40 base pairs in length and correspond to different methylated loci, as well as longer fragments of the same loci that have not been digested into a small fragment because they are not methylated. One of these fragments that are in the range of 20-40base pairs in length corresponds to target fragment 14 of sequence X. In this method, target fragment 14 is selected by ligating adaptor sequence A 16 and adaptor sequence B 18 to its ends. This is done by (i) hybridizing a splint oligonucleotide 20 of formula B'-X'-A' to the fragments of 12 in the presence of the adaptor sequences A 16 and B 18, wherein X', A' and B' are complementary to X, A and B, respectively, to make duplex 21 and (ii) ligating adaptor sequence A 16, the fragment of sequence X 14 and adaptor sequence B 18 to one another to produce a product 22 of formula A-X-B. As would be apparent, splint oligonucleotide 20 and adaptor sequences A 16 and B 18 are designed so that the ends of sequences A 16 and B 18 are ligatably adjacent to the ends of the target fragment of sequence X when they are hybridized to splint oligonucleotide 20 in duplex 21. Splint oligonucleotide 20 and adaptor sequences A 16 and B 18 are shown as duplex 19 in FIG. 1 solely to show which sequences are complementary to one another. In practice, splint oligonucleotide 20 and adaptor sequences A 16 and B 18 are not usually hybridized with one another prior to hybridization with the sample. In practice, the various oligonucleotides can be combined with the digested sample in a single vessel, and the mixture heated and then cooled, thereby denaturing and annealing the various sequences to one another prior to ligation. After ligating adaptor sequence A 16, the fragment of sequence X 14 and adaptor sequence B to one another to produce a product 22 of formula A-X-B, the amount of product 22 can be quantified, thereby providing an estimate of the amount of the methylated locus in nucleic acid sample 2. In particular embodiments, the ligase used may be a thermostable ligase, and the ligation step may be done by cycling the reaction through multiple rounds of denaturation and renaturation, thereby driving the reaction to completion. Quantification of product 22 may be done a variety of different ways, e.g., by quantitative PCR, by sequencing and by digital counting, examples of which are described in greater detail below. In certain embodiments, the splint probes and adaptor sequence may be designed and/or ligated using a method described in UK patent application serial no. 1321191.7, filed on Dec. 2, 2013, which patent application is incorporated by reference herein for disclosure of those methods.

Figure 2:
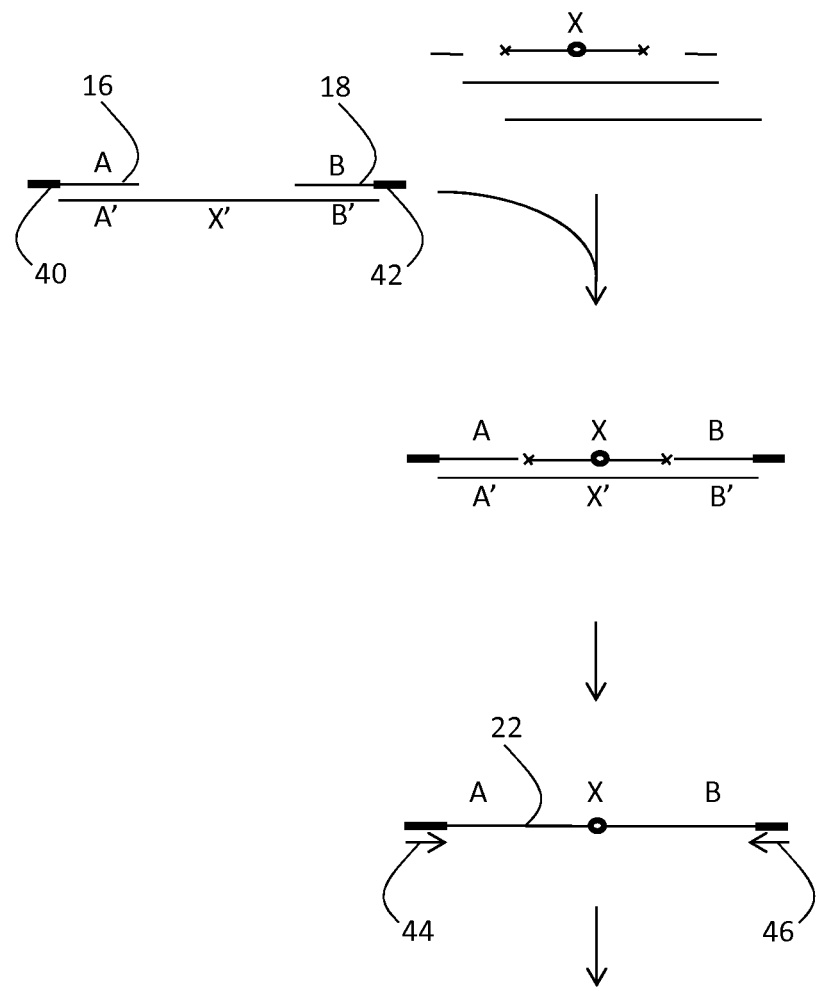
FIG. 2 schematically illustrates some of the features of one implementation of the subject method.

In the embodiment illustrated in FIG. 2, adaptor sequences A 16 and B 18 may be in separate oligonucleotide molecules comprising non-complementary sequences 40 and 42, that provide primer binding sites in product 22. In this embodiment, product 22 can be amplified using primers 44 and 46. In this embodiment, the amount of product 22 can be quantifying by any suitable qPCR assay, e.g., a TaqMan assay or the like. In another embodiment, product 22 may be sequenced (with or without amplification) using primers 44 and 46, or primers that hybridize to tails that have been added to primers 44 and 46, for example. In these embodiments, the amount of product 22 can be estimated by counting the number of sequence reads corresponding to sequence X. In alternative embodiments, non-complementary sequences 40 and/or 42 may contain a molecular barcode and each molecule of product 22 contains a different barcode sequence. In these embodiments, the amount of product 22 can be estimated by counting the number of unique barcode sequences that are associated with the sequence reads corresponding to sequence X.

Figure 3:
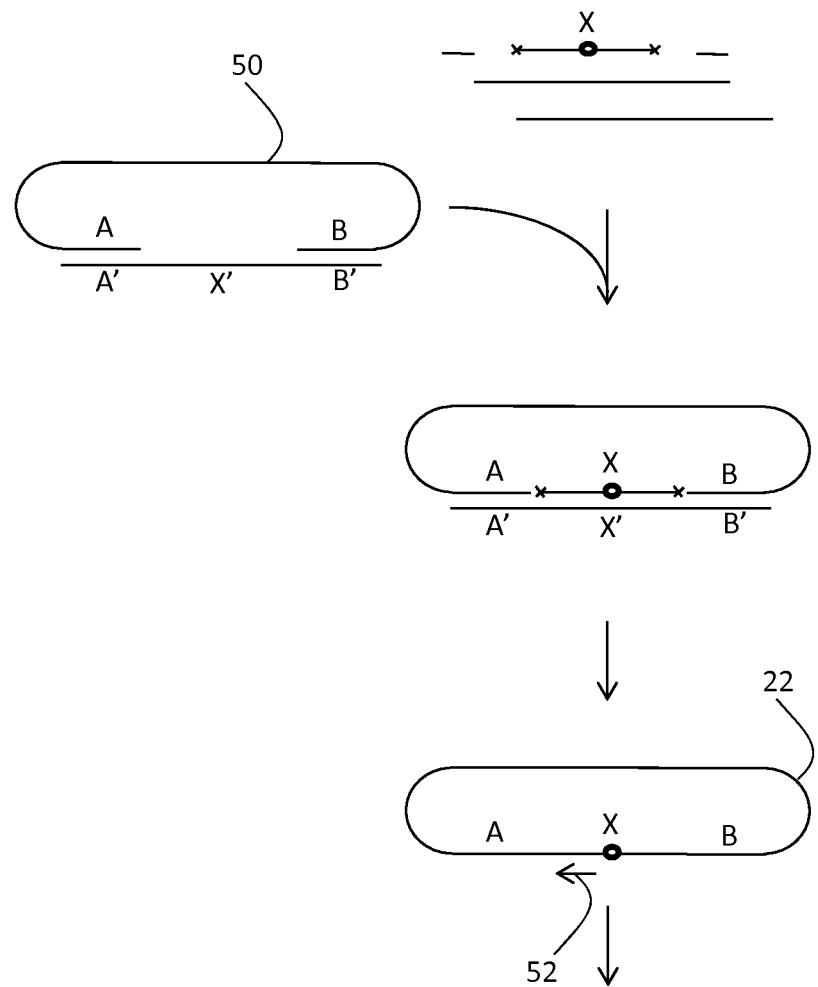
FIG. 3 schematically illustrates some of the features of another implementation of the subject method.

In another embodiment illustrated in FIG. 3, adaptor sequences A and B are present in a single oligonucleotide molecule 50 and product 22 is a circular nucleic acid molecule. In these embodiments, product 22 may be quantified by amplifying the product by rolling circle amplification (RCA) (e.g., using primer 52, which may be complementary to a sequence anywhere in the product) and then estimating the number of RCA products produced. The rolling circle amplification products will contain multiple copies of each of the sequences in product 22. In these embodiments, the quantifying may be done by hybridizing the RCA product to a population of labeled oligonucleotides that hybridize to multiple positions in the RCA product; and individually counting the number of labeled RCA complexes.

Figure 4:
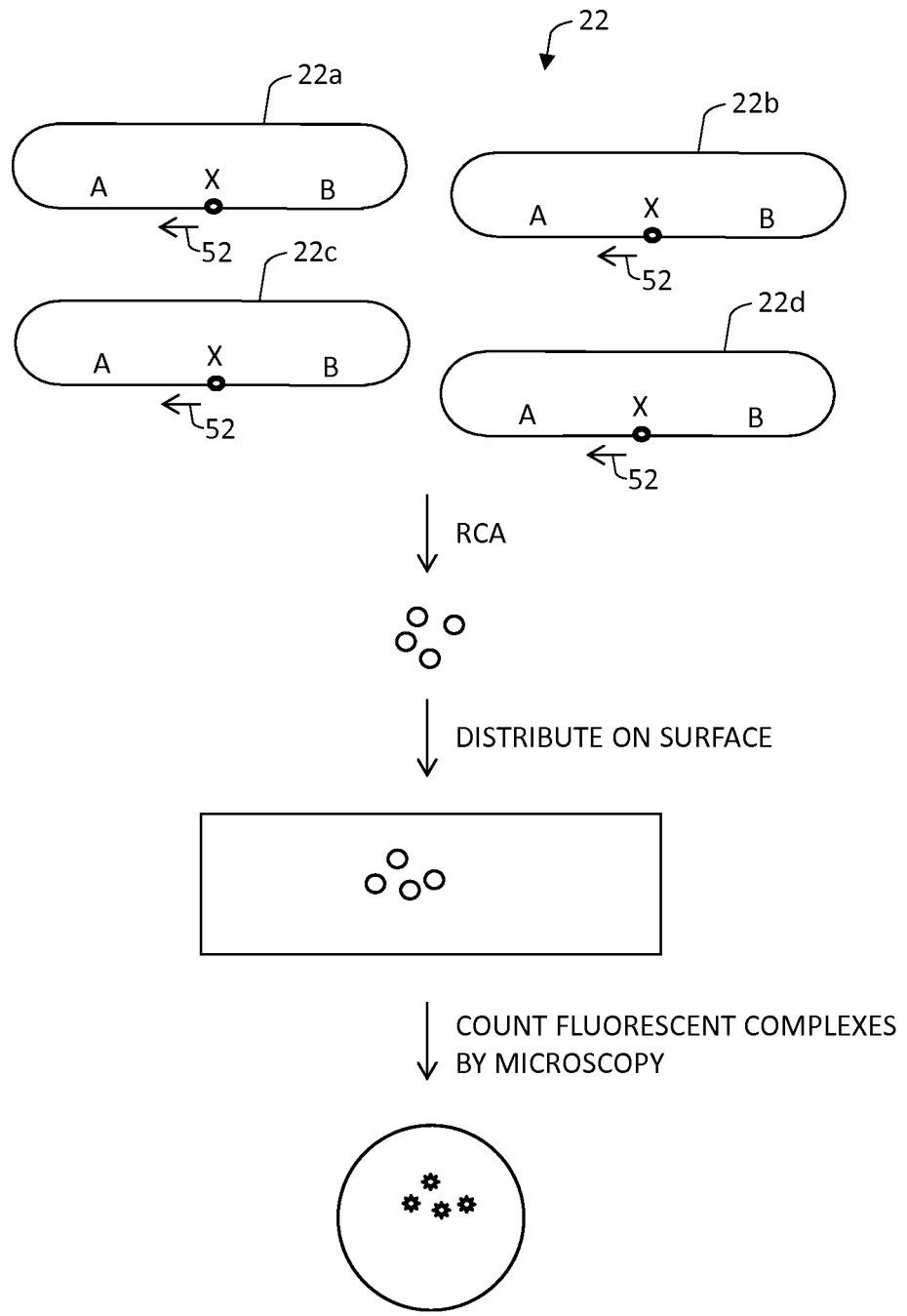
FIG. 4 schematically illustrates a method by which ligation products can be counted.

FIG. 4 illustrates one way by which this embodiment may be implemented. In this implementation, product 22 is composed of four product molecules 22a, 22b, 22c and 22d. In practice, product 22 may be composed of at least 100, at least 1,000 or at least 10,000 or more product molecules of formula A-X-B. In this embodiment, the products are amplified by rolling circle amplification using primer 52 (which may be complementary to a sequence anywhere in the product) to produce a plurality of RCA products. The number of rolling circle amplification products can be estimated by distributing the RCA products on the surface of a support (a slide), hybridizing the RCA products using labeled oligonucleotides (e.g., fluorescently labeled oligonucleotides) and then counting the number of discrete signals in an area of the support by microscopy, e.g., fluorescence microscopy. The labeling can be done before or after the products have been distributed on the support and, because each RCA product contains thousands of copies of the same sequences, there should be thousands of binding sites for the labeled oligonucleotides, thereby increasing the signal. In certain embodiments, the amplification and/or detection methods may be implemented using a method described in UK patent application serial no. 1321196.6, filed on Dec. 2, 2013, which patent application is incorporated by reference herein for disclosure of those methods.

The amount of the methylated locus in the sample may be expressed in a variety of different ways. For example, in some embodiments, the results obtained in the quantification step may be normalized to the amount of input DNA and expressed as a measurement per amount of input DNA (e.g., x number of molecules in y amount of input DNA). This number can provide a useful metric when compared to the amount of other sequences in the same sample. For example, the relative amount (e.g., the percentage) of the methylated locus in the sample may be calculated by comparing the results obtained by the present method to results obtained for a reference locus that is known to be always methylated in the sample. In this example, the amount of the reference locus in the sample can be quantified using a similar method (where the same enzyme or another MspJI family enzyme may be used and the target-specific sequences in the splint oligonucleotide hybridizes to a fragment corresponding to a reference locus, not locus X). In another example, the relative amount (e.g., the percentage) of the methylated locus in the sample may be calculated by comparing the results obtained by the present method to results obtained for a reference locus that is known to be present in the sample. In this example, the amount of the reference locus in the sample can be quantified using a similar method (where an enzyme other than a MspJI family enzyme, e.g., a methylation insensitive enzyme, may be used and the target-specific sequences in the splint oligonucleotide hybridizes to a fragment corresponding to the reference locus, not X). In some embodiments, the absolute amount of methylated locus in the sample can be compared to a standard curve (e.g., a standard curve generated using control samples that contain known amounts of the methylated locus) to provide an estimate of the absolute number of molecules of the methylated locus in the sample.

The lengths of the various regions of the adaptors and splint oligonucleotides may vary greatly depending upon the desired application and how much freight (i.e., how many primer binding sites, barcodes, etc.) are carried by the adaptors. In practice, sequence X' of the splint oligonucleotide will be designed to match the sequence of a fragment that is expected to be generated by digesting a genomic sample with the MspJI family restriction endonuclease being used in the method. For example, if MspJI is used, then sequence X' will be about 32 nucleotides in length and the ends of X will correspond to the cleavage sites for MspJI in genomic DNA. Other MspJI family members create fragments of different lengths and, as such, the length of X' does not need to be about 32 bases if another enzyme, include FspEI, LpnPI, AspBHI, RlaI, and SgrTI, is used. In some cases, X' may be in the range of 25-35 nucleotides in length. Because the recognition sites for these enzymes are known and the sequence of several genomes, including the human genome, are known, the design of splint oligonucleotides can be done by hand or computationally. Depending on the desired application, adaptor sequences A and B may be of 15 to 100 bases (e.g., 18 to 30 bases) in length. As should be readily apparent, the nucleotide sequence of any additional sequences that are appended to the adaptor sequences, e.g., primer binding sites/barcodes, etc., should be designed so that they do not hybridize to the genome under study.

In particular embodiments, one of the adaptor sequences may be linked to an affinity tag, e.g., a biotin moiety, so that, after ligation, the ligation products can be separated from unligated molecules using a solid support comprising a surface tethered capture agent for the affinity tag, thereby binding the ligation products to the solid support and isolating those molecules from other nucleic acids in the sample.

As would be apparent, the primers used in some embodiments may contain sequences that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps.

In some embodiments, the method may be multiplexed to quantify several methylated loci in the sample. This may be done using several splint oligonucleotides, where the sequence corresponding to X is complementary to the loci under investigation. The method may be used to analyze at least 2, at least 5, at least 10, at least 50 or at least 100 different loci in the same reaction.

The method described above can be employed to analyze genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, where in certain embodiments the mammal is a human. In exemplary embodiments, the genomic sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human. In some embodiments, the sample analyzed may be a sample of cell-free DNA obtained from blood, e.g., from the blood of a pregnant female.

In certain embodiments, the subject method may be used to determine the methylation status of a target locus that is associated with a disease, e.g., cancer or a liver disease such as chronic hepatitis or cirrhosis, where the methylation status of locus can be used to diagnose the disease. In these embodiments, source of the genomic DNA may be tissue biopsy or a bodily fluid that contains DNA derived from diseased tissue.

In certain embodiments, the subject method may be used in non-invasive prenatal testing (NIPT) for diagnosis of genetic and epigenetic anomalies in the fetus, including fetal aneuploidies such as trisomy 21, trisomy 18 and trisomy 13; imprinting disorders such as Beckwith-Wiedemann syndrome, Prader-Willi and Angelman syndromes, and Albright's Hereditary Osteodystrophy; and other genetic defects, such as Fragile X Syndrome. For instance, hypermethylation of the following loci may be diagnostic: CpG islands around CRYAA, HLCS, C21orf63, OLIG2, CBR1, SIM2, DSCAM, TRPM2, C21orf29, MIR155HG, ICOS ligand-like, SIM2, DSCR6, chr21 group00165, PRMT2 and COL18A1 for trisomy 21 (Lim et al., BMC Med Genomics, 2014 7:1; Tong et al., Clin Chem, 2009 56:90; Tong et al., PLoS One, 2010 5:e15244; Chim et al., Clin Chem, 2008 54:500; U.S. Pat. No. 8,476,013); hypermethylated CpG sites in the promoter sequence of SERPINB5 (maspin), between the VAPA and APCDD1 genes, and CpG sites in CIDEA, chr18 group00091, chr18 group00094, KLHL14, ST8SIA3, ONECUT2, RAX, chr18 group00277, NETO1, MBP and NFATC1 for trisomy 18 (Tong et al., Clin Chem, 2006 52:2194; Tsui et al., PLoS One, 2010 5:e15069; U.S. Pat. No. 8,476,013); hypermethylation sites in chr13 group00016, ATP8A2, GSJ1, PDX1, MAB21L1, RB1, PCDH17, KLHL1, POU4F1, GPC6, SOX21, ZIC2, chr13 group00385, chr13 group00390, chr13 group00391, chr13 group00395, chr13 group00399 and PROZ for trisomy 13 (U.S. Pat. No. 8,476,013); CpG hypermethylation sites at 11p15.5 for Beckwith-Wiedemann Syndrome (Coffee et al., Genet Med, 2006 8:628); 15q11.2-q13 for Prader-Willi and Angelman syndromes (Procter et al., Clin Chem, 2006 52:1276); the XL locus associated with Albright's Hereditary Osteodystrophy (Izzi et al., PLoS ONE, 2012 7:e38579); and CpG sites in the FMR1 gene for Fragile X Syndrome (Hansen et al., Hum Mol Genet, 1992 1:571; Alisch et al., BMC Med Genet, 2013 14:18). Thus, a splint oligonucleotide of the subject method may be designed to be complementary to the hypermethylated sites of these loci to diagnose prenatal genetic and epigenetic anomalies.

In certain embodiments, the present method may be used for NIPT. For instance, hypermethylated sequences in the promoter region of the RASSF1A gene may be used to improve prenatal RhD genotyping and detection of susceptibility to preeclampsia (Chan et al., Clin Chem, 2006 52:2211; Tsui et al., Prenat Diagn, 2007 27:1212). As such, a splint oligonucleotide of the subject method may be designed to be complementary to the methylated sequences in the promoter region of the RASSF1A gene. RASSF1 (Ras association (RalGDS/AF-6) domain family 1) was found to be hypermethylated in placenta but completely unmethylated in maternal blood cells.

In certain embodiments, the present method may be used to detect hypermethylation in fetal DNA by designing a splint oligonucleotide complementary to methylated sequences in or associated with the following genes: SOX14, TBX3, SIX2, TLX3, FOXP4, NPY, SHH, OSR2, GLIS3, PRMT8, PAX9, SIX1, ISL2, DLX4, CBX4 and EDG6 (Nygren et al., Clin Chme, 2010, 56: 1627; U.S. Pat. No. 8,476,013).

In yet other embodiments, the present method may be used to diagnose susceptibility to pathological pregnancies, such as preeclampsia. For example, hypermethylation in CpG sites in the c-myc promoter region and exon 1 of H19 of fetal DNA are associated with preeclampsia (Rahat et al., Mol Hum Reprod, 2014; Lu et al., Int J Mol Med, 2014). Thus in certain embodiments, a splint oligonucleotide of the subject method designed to be complementary to the methylated sequences in these regions may be used for determining predisposition to preeclampsia.

In certain embodiments, the subject method may be employed as part of a cancer diagnostic. For example, colorectal cancer is associated with increased methylation of CpG islands in or around several genes, including BMP3

NDRG4, Septin 9, TFPI1, TFPI2, p14, EYA2, ALX4, IGFBP7, GATA4/5, MGMT, TBX5, ID4, BTG4, miRNA-34b/c, CDH13, TPEF/HPP1, NPY, PENK, WIF, EN1, SCTR, INHBB and Vimentin (Zou et al., Cancer Epidemiol Biomarkers Prev, 2007 16:2686; Melotte et al., J Natl Cancer Inst, 2009 101:916; Grützmann et al., PLoS One, 2008 3:e3759; DeVos et al., Clin Chem, 2009, 55:1337; Wasserkort et al., BMC Cancer, 2013 13:398; Hibi et al., Cancer Lett, 2011 311:96; Esteller et al., Cancer Res, 2000 60:129; Zou et al., Cancer Epidemiol Biomarkers Prev, 2007 16:2686; Hinoue et al., PLoS One 2009 4:e8357; Hellebrekers et al., Clin Cancer Res, 2009 15:3990; Shen et al., J Natl Cancer Inst, 2005 97:1330; Yu et al., Oncogene, 2010 29:6464; Clin Cancer res, 2004 10:7475; Toyota et al., Cancer Res, 2008 68:4123; Toyooka et al., Cancer Res, 2002 62:3382; Ebert et al., Neoplasia, 2005, 7:771; Chen et al., J Natl Cancer Inst, 2005 97:112, Cancer Epidemiol Biomarkers Prev, 2007 16:2686; Roperch et al., BMC Cancer, 2013 13:566; Mayor et al., Br J Cancer, 2009 100:1534). As such, in certain embodiments, the splint oligonucleotide used in the subject method may be designed to be complementary to a methylated sequence in those genes.

Hepatocellular carcinoma and/or liver cirrhosis and/or hepatitis C virus infection is correlated with increased methylation of CpG islands associated with p16, p15, RASSF1A, SSBP2, B4GALT1, CASP8, SOCS1, the D17S5 locus of HIC-1, APC, WIF-1, RUNX-3, DLC-1, SFRP-1, DKK, CDH1, KLK10, OCGR1, DUSP4, NPR1, CYP24A1, CDKN2A, CCNA1, GSTP1, p14, p73, RAR-β, AR, DBCCR1, IRF7 and OCT6 (Wong et al., Cancer Res, 1999 59:71; Chu et al., J Korean Med Sci, 2004 19:83; Wong et al., Clin Cancer Res, 2000 6:3516; Michailidi et al., Gastroenterol Res Pract, 2014 2014:597164; Yu et al., BMC Cancer, 2002 2:29; Yoshikawa et al., Nat Genet, 2001 28:29; Kanai et al., Hepatology, 1999 29:703; Liu et al., World J Gastroenterol, 2011 17:4718; Mah et al., Biomark Res, 2014 2:5). As such, in certain embodiments, the splint oligonucleotide used in the subject method may be designed to be complementary to a methylated sequence in these regions.

Likewise, multiple myeloma is associated with increased methylation of CpG islands in the promoter regions of p16 and SOCS-1 (Merlo et al., Nat Med, 1995 1:686; Lo et al., Cancer Res, 1999 59:3899; Wong et al., Clin Cancer Res, 2003 9:1047; Galm et al., Blood, 2003, 101:2784). As such, in certain embodiments, the splint oligonucleotide used in the subject method may be designed to be complementary to a methylated promoter sequence in those genes. In addition, multiple forms of leukemia are associated with hypermethylation in p15, p16, p14, p53, DAPK, NES-1, ADAMTS5, WIF-1, sFRP-1, MYOD1, PTPRZ1, PPARG, FOXE3, FBXO39, PKDREJ, TCF3, EGR4, BTG4, PAX5, IKZF1, TLX3, RAG1, POU2AF1, COBL, COL6A2, CPVL, DFNB31, EYA4, FAM24B, FAT1, FUCA2, INADL, MYO3A, PCDHGA12, PON3, ROR1, SYNM, TNIK, ZNF502, CDKN2A, PTPRO, CSMD1, ABI3, SCGB2A1, VHL, GPX3, IGSF4, SERPIND5, ADORA3, AIRE, CARD15, LOC340061, UNC5CL, LDOC1, PRF1, FABP7, SOX11, DLX1, FAM62C, SOX14, RSPO1, ADCY5, HAND2, SPOCK, MLL, ING1, PRIMA1, BCL11B, LTBP2, BNC1, NR2F2, SALL1, GALGT2, LHX1, DLX4, KLK10, TFAP2, APP, FLJ21062, BNIP3, MGMT, RBP1, GATA4, CRABP1, LANCL1, KCNK12, SORL1, CXorf57, SOX9, KIAA0746, ASPHD2, ARHGAP17, PMM2, IL12A, JDP2, PAK1, GALNS, FGD2, LYAR, HOXA9, AHR, ROBO1, NPTX2, CDH1, CDKN2B, HOXD8, MLF-1, PCDH8, CD44, GADD45, ZMAT3, IRF7, KLF6 and p73 (Bodoor et al., Asian Pac J Cancer Prev, 2014 15:75; Zhao et al., Biomark Res, 2013 1:24; Martinez-Delgado et al., Int J Cancer, 2002 102:15). Thus, in certain embodiments, the splint oligonucleotide used in the subject method may be designed to be complementary to a methylated sequence in those genes.

Likewise, cholangiocarcinoma is associated with hypermethylation of CpG islands associated with OPCML, SFRP1, HIC1, PTEN and DcR1 (Sriraksa et al., Br J Cancer, 2011 104:1313). As such, in certain embodiments, the splint oligonucleotide used in the subject method may be designed to be complementary to the methylated CpG islands of these genes.

Furthermore, lung cancer is associated with increased methylation of CpG islands in the promoter regions of p16, DAP kinase, MGMT, SRBC, GSTP1 (Belinski et al., Proc Natl Acad Sci, 1998 95:11891; Esteller et al., Cancer Res, 1999 59:67; Esteller et al., Cancer Res, 1999 59:67; Esteller et al., Proc Am Assoc Cancer Res, 1998 39:92; Zöchbauer-Müller et al., Oncogene, 2005 24:6249; Esteller et al., Cancer Res, 1999 59:67; Jain et al., PLoS One, 2012 7:e35789). As such, in certain embodiments, the splint oligonucleotide used in the subject method may be designed to be complementary to a methylated sequence associated with these loci.

In addition, breast cancer is associated with hypermethylation of CpG islands in SFRP1, SFRP2, SFRP 5, BRCA1, LKB1, ER, PR, SYK, RIZ1, GSTP1 (Veeck et al., Oncogene, 2006 25:3479; Veeck et al., Mol Cancer, 2008 7:83; Veeck et al., Carcinogenesis, 2008 29:991; Esteller et al., J Natl Cancer Inst, 2000 92:564; Esteller et al., Cancer Res, 2001 61:3225; Esteller et al., Oncogene, 2000 19:164; Ottaviano et al., Cancer Res, 1994 54:2552; Lapidus et al., Clin Cancer Res, 1996 2:805; Yuan et al., Cancer Res, 2001 61:5558; Du et al., Cancer Res, 2001 61:8094; Esteller et al., Cancer Res, 1998 58:4515). As such, in certain embodiments, the splint oligonucleotide used in the subject method may be designed to be complementary to a methylated sequence in or to a methylated sequence associated with these genes.

Likewise, renal carcinoma is associated with increased methylation of CpG islands in the promoter regions of GSTP1 and VHL (Esteller et al., Cancer Res, 1998 58:4515; Herman et al., Proc Natl Acad Sci, 1994 91:9700); endometrial carcinoma is associated with increased methylation in the promoter regions of hMLH1 (Esteller et al., Am J Pathol, 1999 155:1767); and esophageal adenocarcinoma is associated with hypermethylation in the promoter regions of APC (Kawakami et al., J Natl Cancer Inst, 2000 92:1805). Thus, in certain embodiments, the splint oligonucleotide used in the subject method may be designed to be complementary to a methylated sequence in or to a methylated sequence in the promoter regions of these genes.

Furthermore, oral squamous cell carcinoma is associated with hypermethylation in KIF1A, HOXA9, NID2, EDNRB, p16, RARβ, CDH-1, CYGB and CYCA1 (Guerrero-Preston et al., Cancer Prev Res (Phila), 2011 4:1061; Shaw et al., Br J Cancer, 2006 94:561); while hypermethylation in EDNRB and DCC are associated with premalignant or malignant oral lesions (Pattani et al., Cancer Prev Res (Phila), 2010 3:1093; Schussel et al., Clin Cancer Res, 2013 19:3268). As such, in certain embodiments, the splint oligonucleotide used in the subject method may be designed to be complementary to a methylated sequence in the promoter regions of these genes. In addition, esophageal squamous cell carcinoma is associated with increased methylation of 5' regulatory regions of miRNAs, including miR-34a, miR-34b/c and miR-129-2 (Chen et al., Int J Cancer, 2012 130:1607). Thus, in certain aspects, the splint oligonucleotide used in the subject method may be designed to be complementary to a methylated sequence in the 5' regulatory regions of these miRNAs. Esophageal squamous cell carcinoma is also associated with increased methylation in GPX3 (He et al., Dig Dis Sci, 2011 56:681); and ECRG4 (Yue et al., World J Gastroenterol, 2003 9:1174). As such, in certain embodiments, the splint oligonucleotide used in the subject method may be designed to be complementary to a methylated sequence in the promoter regions of these genes.

Likewise, vulvar squamous cell carcinoma is associated with hypermethylation in MGMT, RASSF2A and TSP-1 (Guerrero et al., Int J Cancer, 2011 128:2853). As such, in certain embodiments, the splint oligonucleotide used in the subject method may be designed to be complementary to a methylated sequence in the promoter regions of these genes. Epstein-Barr virus-associated gastric carcinomas is associated with hypermethylation at loci such as MINT2, MINT31, p14, p16, p73, and RUNX3 (Saito et al., J Med Virol, 2013 85:121). Thus the splint oligonucleotide used in the subject method may be designed to be complementary to a methylated sequence at those loci.

In addition, prostate cancer is associated with hypermethylation in GSTP1, AR, TIMP2 (Lee et al., Proc Natl Acad Sci, 1994 85:11733; Jarrard et al., Cancer Res, 1998 58:5310; Pulukuri et al., Oncogene, 2007 26:5229). As such, in certain embodiments, the splint oligonucleotide used in the subject method may be designed to be complementary to a methylated sequence in these genes. Retinoblastoma is associated with hypermethylated promoter sequences of genes, such as Rb (Stirzaker et al., Cancer Res, 1997 57:2229). Therefore, the splint oligonucleotide used in the subject method may be designed to be complementary to a methylated sequence in the promoter regions of these genes. Likewise, glioblastoma multiforme is associated with hypermethylation of CpG sites in the 5' regulatory region of THBS1 (Li et al., Oncogene, 1999 18:3284). In certain embodiments, the splint oligonucleotide used in the subject method may be designed to be complementary to a methylated sequence in these genes.

In some embodiments, the subject method may be employed to diagnose neurodegenerative disorders. For instance, hypermethylation of CpG sites at C9orf72 is associated with amyotrophic lateral sclerosis and frontotemporal lobar degeneration (Xi et al., Am J Hum Genent, 2013 92:981; Xi et al., Am J Hum Genent, 2014). Thus in certain embodiments, a splint oligonucleotide of the subject method may be designed to be complementary to a methylated sequence in CpG sites of C9orf72. Likewise, increased methylation at CpG sites at the following genes are associated with Parkinson's Disease: KCTD5, VAV2, MOG, TRIM10, HLA-DQA1, ARHGEF10, GFPT2, HLA-DRB5, TMEM9, MRI1, MAPT, HLA-DRB6, LASS3, GSTTP2, GSTTP1 (Masliah et al., Epigenetics 2013 8:1030; Coupland et al., Mov Diord, 2013). As such, a splint oligonucleotide of the subject method may be designed to be complementary to a methylated sequence in the CpG sites of those genes.

As noted above, in some cases the sample analyzed may be a sample of cell-free DNA obtained from blood, e.g., from the blood of a pregnant female. In these embodiments, the method may be used to detect chromosome abnormalities in the developing fetus (as described above) or to calculate the fraction of fetal DNA in the sample, for example. These embodiments provide for the detection and quantification of fetal nucleic acid in a maternal sample based on the methylation status of the nucleic acid in the sample. In some cases, the amount of fetal nucleic acid from a maternal sample can be determined relative to the total amount of nucleic acid present, thereby providing the percentage of fetal nucleic acid in the sample. In some cases, the copy number of fetal nucleic acid can be determined in a maternal sample. In some cases, the amount of fetal nucleic acid can be determined in a locus-specific manner and sometimes with sufficient sensitivity to allow for accurate chromosomal dosage analysis (for example, to detect the presence or absence of a fetal aneuploidy). In some cases, the method can be used to determine the concentration of fetal DNA in a maternal sample, for example, by the following method: a) determining the total amount of DNA present in a maternal sample; determining the amount of a methylated fetal marker in the material sample using the present method; and comparing the amount of total DNA to the amount of the fetal maker DNA. The concentration of fetal DNA in the maternal sample can be extrapolated from these results. In some cases, the absolute copy number of fetal nucleic acid in a maternal sample can be determined.

In particular embodiments, a method of estimating the fetal fraction in a sample of cell-free DNA obtained from the blood of a pregnant female is provided. In some cases, this method comprises; (a) digesting said sample with an MspJI family restriction endonuclease to produce a population of fragments that are in the range of 20-40 base pairs in length and have a central methylated cytosine; (b) ligating adaptor sequence A and adaptor sequence B to the respective ends of a plurality of target fragments that are only methylated in fetal DNA, by: (i) hybridizing a plurality of splint oligonucleotide of formula B'-X'-A' to the fragments of (a) in the presence of the adaptor sequences A and B, wherein A' and B' are complementary to A and B, respectively, and sequence X' varies between the different splint oligonucleotides and each sequence X' is complementary to a target fragment that is only methylated in fetal DNA; and (ii) ligating adaptor sequence A, sequence X and adaptor sequence B to one another to produce products of formula A-X-B; and (c) quantifying the amount of products of formula A-X-B, and (d) normalizing the amount obtained in (c) to the amount of control locus in the sample, wherein said normalizing provides an estimate of the fetal fraction in the sample. In some cases, this method may be implemented using at least 100, at least 200, at least 300, at least 500 or at least 1,000 or more different splint oligonucleotides, where each splint oligonucleotide is complementary to a sequence that is only methylated in fetal DNA. In these cases, the fetal fraction can estimated by, e.g., comparing the normalized amount obtained in (d) to a standard curve. In some cases, the control locus may be on one or more of chromosomes 21, 18 and 13. In some cases, the amount of ligation product quantified in (c) may be compared to the amount of a control locus that is not differentially methylated in the sample.

In certain embodiments, the double stranded DNA being analyzed may be derived from a single source (e.g., a single subject, etc.), whereas in other embodiments, the nucleic acid sample may be a pool of nucleic acids extracted from a plurality of sources (e.g., a pool of nucleic acids from a plurality of subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed.

Kits

Also provided by this disclosure are kits for practicing the subject methods, as described above. In some embodiments, a kit may contain at least: (a) an MspJI family restriction endonuclease; (b) adaptor sequence A and adaptor sequence B; (c) a splint oligonucleotide of formula B'-X'-A', wherein X', A' and B' are complementary to X, A and B, respectively, and X is a genomic sequence of 20-40 base pairs in length and has a central cytosine that is differentially methylated; and (d) a ligase. In some embodiments, the adaptor sequences A and B may be present in the same oligonucleotide molecule. The various components of the kit may be present in separate containers or certain compatible components may be precombined into a single container, as desired.

In addition to the above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The invention claimed is:

1. A method of estimating the amount of a methylated locus in a sample, comprising:
   (a) digesting a nucleic acid sample that contains both unmethylated and methylated copies of a genomic locus with an MspJI family restriction endonuclease to produce a population of fragments that are in the range of 20-40 base pairs in length and have a central methylated cytosine, wherein the population of fragments comprises a target fragment of sequence X;
   (b) ligating adaptor sequence A and adaptor sequence B to the respective ends of the target fragment of sequence X by:
      (i) hybridizing a splint oligonucleotide of formula B'-X'-A' to the fragments of (a) in the presence of the adaptor sequences A and B, wherein X', A' and B' are complementary to X, A and B, respectively, and
      (ii) ligating adaptor sequence A, sequence X and adaptor sequence B to one another to produce a product of formula A-X-B; and
   (c) quantifying the amount of ligation products of formula A-X-B, thereby providing an estimate of the amount of the methylated locus in the nucleic acid sample.

2. The method of claim 1, wherein the MspJI family restriction endonuclease is MspJI.

3. The method of claim 1, wherein the quantifying is done by sequencing.

4. The method of claim 1, wherein the quantifying is done by qPCR.

5. The method of claim 1, wherein adaptor sequences A and B are present in the same oligonucleotide molecule and the product of step (b) is a circular nucleic acid molecule.

6. The method of claim 5, wherein the quantifying is done by:
   (i) amplifying the circular nucleic acid molecule by rolling circle amplification (RCA),
   (ii) hybridizing the RCA product to a population of labeled oligonucleotides that hybridize to multiple positions in the RCA product to produce labeled RCA complexes; and
   (iii) individually counting the number of labeled RCA complexes.

7. The method of claim 1, wherein methylation of said locus is associated with a disease.

8. The method of claim 7, wherein methylation of said locus is associated with cancer.

9. The method of claim 8, wherein said locus is that of BMP3, TFPI1, NDRG4, Septin 9, TFPI2, or Vimentin.

10. The method of claim 7, wherein methylation of said locus is associated with a liver disease.

11. The method of claim 1, wherein the sample is a sample of cell-free DNA obtained from blood.

12. The method of claim 1, wherein the sample is a sample of cell-free DNA obtained from the blood of a pregnant female and the methylated locus is only methylated in fetal DNA.

13. The method of claim 12, wherein the amount of the methylated locus in the nucleic acid sample is used to calculate the fraction of fetal DNA in the sample.

14. A method of estimating the fetal fraction in a sample of cell-free DNA obtained from the blood of a pregnant female, comprising:
   (a) digesting said sample with an MspJI family restriction endonuclease to produce a population of fragments that are in the range of 20-40 base pairs in length and have a central methylated cytosine, wherein the population of fragments comprises a target fragment of sequence X that is only methylated in fetal DNA;
   (b) ligating adaptor sequence A and adaptor sequence B to the respective ends of a plurality of target fragments that are only methylated in fetal DNA, by:
      (i) hybridizing a plurality of splint oligonucleotides of formula B'-X'-A' to the fragments of (a) in the presence of the adaptor sequences A and B, wherein A' and B' are complementary to A and B, respectively, and sequence X' varies between the different splint oligonucleotides and each sequence X' is complementary to the target fragment of sequence X that is only methylated in fetal DNA; and
      (ii) ligating adaptor sequence A, sequence X and adaptor sequence B to one another to produce products of formula A-X-B;
   (c) quantifying the amount of products of formula A-X-B, and
   (d) normalizing the amount obtained in (c) to the amount of one or more control loci in the sample, wherein said normalizing provides an estimate of the fetal fraction in the sample.

15. The method of claim 14, wherein the method comprises comparing the normalized amount obtained in (d) to a standard curve.

16. The method of claim 14, wherein the one or more control loci is on one or more of chromosomes 21, 18 and 13.

17. The method of 14, wherein the one or more control loci of step (d) are not differentially methylated in the sample.

\* \* \* \* \*